US011992696B2

(12) United States Patent
Johnson et al.

(10) Patent No.: US 11,992,696 B2
(45) Date of Patent: May 28, 2024

(54) INTRAORAL PHOTOTHERAPY APPARATUS AND METHODS FOR TREATMENT OF BRUXISM

(71) Applicant: PerioTech, LLC, Palm Beach Gardens, FL (US)

(72) Inventors: Richard Johnson, Palm Beach Gardens, FL (US); Nicholas Puro, Sunny Isles Beach, FL (US)

(73) Assignee: PerioTech, LLC, Palm Beach Gardens, FL (US)

( * ) Notice: Subject to any disclaimer, the term of this patent is extended or adjusted under 35 U.S.C. 154(b) by 107 days.

(21) Appl. No.: 17/587,997

(22) Filed: Jan. 28, 2022

(65) Prior Publication Data
US 2023/0241408 A1 Aug. 3, 2023

(51) Int. Cl.
*A61N 5/06* (2006.01)
*A61N 5/067* (2006.01)

(52) U.S. Cl.
CPC ......... *A61N 5/0613* (2013.01); *A61N 5/0603* (2013.01); *A61N 5/067* (2021.08); *A61N 2005/0606* (2013.01); *A61N 2005/0626* (2013.01); *A61N 2005/0652* (2013.01); *A61N 2005/0659* (2013.01); *A61N 2005/0663* (2013.01)

(58) Field of Classification Search
CPC ..... A61N 5/0613; A61N 5/067; A61N 5/0603
USPC .......................................................... 607/89
See application file for complete search history.

(56) References Cited

U.S. PATENT DOCUMENTS

| 7,270,657 B2 | 9/2007 | Rizoiu et al. |
| 7,751,895 B2 | 7/2010 | Jones et al. |
| 9,730,780 B2 | 8/2017 | Brawn et al. |
| 2006/0149342 A1 | 7/2006 | Huang et al. |
| 2007/0031776 A1* | 2/2007 | Sakaguchi ........... A61C 19/066 433/29 |
| 2012/0148976 A1 | 6/2012 | Brawn |
| 2017/0080249 A1* | 3/2017 | Brawn ................ A61N 5/0603 |
| 2017/0135781 A1 | 5/2017 | Gregg, II |
| 2018/0140864 A1 | 5/2018 | Brawn |
| 2019/0083809 A1 | 3/2019 | Zhang |
| 2020/0268439 A1 | 8/2020 | Frazier et al. |

(Continued)

FOREIGN PATENT DOCUMENTS

WO    WO 2018/026892 A1    2/2018

OTHER PUBLICATIONS

Wetselaar et al "The prevalence of awake bruxism and sleep bruxism in the Dutch adult population", *Journal of Oral Rehabilitation*, 46: 617-623 (Feb. 2019).

(Continued)

*Primary Examiner* — Nadia A Mahmood
(74) *Attorney, Agent, or Firm* — Finnegan, Henderson, Farabow, Garrett & Dunner LLP

(57) ABSTRACT

A device and method for treating sleep and awake bruxism includes an intraoral phototherapy device having a mouthpiece for delivering light radiation. Instructions are provided for waking using the intraoral phototherapy device by placing the mouthpiece at the treatment area and applying light radiation during a predetermined number of sessions throughout a predetermined treatment period wherein the incidence of awake and sleep bruxism is decreased compared to without light treatment.

17 Claims, 6 Drawing Sheets

(56) References Cited

U.S. PATENT DOCUMENTS

2021/0267738 A1 9/2021 Mackie
2022/0008743 A1 1/2022 Johnson

OTHER PUBLICATIONS

Jiménez-Silva et al "Sleep and awake bruxism in adults and its relationship with temporomandibular isorders: A systematic review from 2003 to 2014", *Acta Odontologica Scandinavica*, 75:1, 36-58 (Oct. 2016).

Abidi et al "Management of TMD Symptoms with Photobiomodulation Therapy" *New York State Dental Association* https://issuu.com/brownst303/docs/nysd_november_final_20/s/11325735 on (Nov. 2020).

James "Bruxism: The Grind of the Matter" *Dentalcare.com* https://www.dentalcare.com/en-us/professional-education/ce-courses/ce485/overview (Jan. 2022).

International Search Report and Written Opinion from International Application No. PCT/US2022/82595 dated Apr. 27, 2023 (8 pages).

Kobayashi, Fernanda Yukie et al., "Evaluation of the effectiveness of infrared light-emitting diode photobiomodulation in children with sleep bruxism", *Medicine*, (2019) 98:38, pp. 1-5.

Kobayashi, Fernanda Yukie et al., "Immediate Evaluation of the Effect of Infrared LED Photobiomodulation on Childhood Sleep Bruxism: A Randomized Clinical Trial", *Life*, (2022) 12,964, 10 pages.

Salgueiro, Monica da Consolação Canuto et al., "Effect of Photobiomodulation on Salivary Cortisol, Masticatory Muscle Strength, and Clinical Signs in Children with Sleep Bruxism: A Randomized Controlled Trial", *Photobiomodulation, Photomedicine, and Laser Surgery*, vol. 39, No. 1 (2021), pp. 23-29.

* cited by examiner

INTRAORAL PHOTOTHERAPY APPARATUS AND METHODS FOR TREATMENT OF BRUXISM

TECHNICAL FIELDS

This disclosure concerns treatments of bruxism, more specifically, a method to facilitate the relaxation of muscles and tissues proximal to the temporomandibular joint using phototherapy apparatus.

BACKGROUND

Bruxism is the grinding, gnashing, or clenching of the teeth. It is usually an unconscious activity that can occur during sleep (sleep bruxism) and during wakefulness (awake bruxism). While it is not completely understood what causes sleep bruxism, it may be due to a combination of physical, psychological, and genetic factors. Stress, medications, lifestyle habits, and occlusion are major contributors to grinding during sleep. Awake bruxism may be linked to emotions such as anxiety, stress or a habit during deep concentration. It is reported that clinical experience indicates a lack of patient awareness and reporting of both awake bruxism and sleep bruxism. A dentist can diagnose bruxism by examining the teeth and mouth for changes such as abnormal broken or missing teeth and tenderness in the jaw muscles.

Grinding and clenching of teeth by sleep bruxism and awake bruxism can cause loss of tooth tissue. The teeth will appear flattened from wear down of the occlusal surfaces of the enamel, reduction of the crown height, exposing the dentin that increases the risks of sensitivity, decay, and discoloration. Excessive grinding and clenching can result in fractured, chipped, or loose teeth and damage to the periodontium.

There is a difference in bruxism when asleep and awake. Sleep bruxism is a masticatory muscle activity when sleeping, characterized as either rhythmic (phasic) or non-rhythmic (tonic). Whereas awake bruxism is a masticatory muscle activity when awake characterized by repetitive or sustained tooth contact that may also involve bracing or thrusting of the mandible. Both types of bruxism can affect the muscles of the orofacial structure. Bruxism involves excessive muscle use by applying long-time stress to the muscle fibers. This can lead to soreness, inflammation, and tightness that produce pain in and around the muscles of the jaw and temporomandibular joint (TMJ), such as the hamular notch of the maxilla or the retromolar pad of the mandible. If untreated, it can develop into temporomandibular disorders (TMD) that lead to headaches, ear pain, tinnitus, neck pain, and shoulder pain, in addition to jaw pain or a locked jaw that won't open completely. Excessive sleep bruxism can be loud enough to wake you up and cause sleep disruption.

The goals of bruxism treatment are to reduce the pain, prevent permanent irreversible damage to the teeth and surrounding structures, and reduce incidence of sleep and awake bruxism as much as possible. Methods of decreasing the incidence of sleep and awake bruxism include a wide range of interventions or treatments and muscle relaxation exercises are one of them. When grinding the teeth, it is known that usually the masseter muscle is sore and inflamed. Muscle relaxation exercises can reduce the tension and pain while also improving the blood and nourishments circulation to help treat and reduce muscle soreness and/or inflammation. It is typically conducted by a therapist with repeated treatments which can be time-consuming and expensive. Therefore, it is desired to have a convenient intraoral muscle relaxation and pain relief method so the treatment can be more convenient, and the outcome can be better secured.

SUMMARY

According to an exemplary embodiment of the present disclosure, a method for the treatment of bruxism is described. The method includes identifying a patient having bruxism, providing the patient with an intraoral phototherapy device having a flexible mouthpiece for directing the light to the treatment area, and providing instructions for using the intraoral phototherapy device. The instruction includes placing and adjusting the mouthpiece over the treatment area and applying a light therapy during a predetermined number of sessions throughout a predetermined treatment period to the patient while awake. The incidence of bruxism is less than without phototherapy treatment.

According to yet another exemplary embodiment of the present disclosure, a method for the treatment of bruxism is described. The method includes identifying a patient having exhibited or manifested a bruxism symptom, e.g., soreness or tightness in the tissues proximal to the hamular notch of the maxilla and/or the retromolar pad of the mandible, providing the patient with an intraoral phototherapy device having a flexible mouthpiece for directing the light to the treatment area, and providing instructions for waking using the intraoral phototherapy device. The method includes providing instructions includes placing and adjusting the mouthpiece over the treatment area and applying light therapy during a predetermined number of sessions throughout a predetermined treatment period to the patient while awake. The bruxism symptom has decreased faster than without phototherapy treatment.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

BRIEF DESCRIPTION OF THE DRAWINGS

The accompanying drawings constitute a part of this specification. The drawings illustrate several embodiments of the present disclosure and, together with the description, serve to explain the principles of the disclosed embodiments as set forth in the accompanying claims.

The drawings are not necessarily to scale or exhaustive. Instead, emphasis is generally placed upon illustrating the principles of the inventions described herein. The accompanying drawings, which are incorporated in and constitute a part of this specification, illustrate several embodiments consistent with the disclosure and together with the description, serve to explain the principles of the disclosure. In the drawings.

Reference will now be made in detail to exemplary embodiments. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

DETAILED DESCRIPTION

It is to be understood that both the foregoing general description and the following detailed description are exemplary and explanatory only and are not restrictive of the claims.

The disclosed embodiments relate to devices, systems, and methods for the treatment of sleep bruxism and awake bruxism. Advantageously, embodiments of the present disclosure can be implemented to lower the incidence of sleep bruxism and awake bruxism than without. Advantageously, embodiments of the present disclosure can be implemented to relax the stressed muscles of the treatment area. Further advantageously, embodiments of the present disclosure can be implemented to relief the symptoms around the TMJ caused by bruxism.

Compared to without treatment, an intraoral phototherapy with light sources such as low-level laser therapy (LLLT) or light emitter diodes (LED) with plurality of emitters can decrease the incidence of sleep and awake bruxism, increase the speed of relieving muscle pain associated with bruxism, relax the contracted muscles, and generally reduce the probability of TMJ issues developing into TMD. Effective treatment of bruxism can further help to prevent symptoms like headaches, ear pain, tinnitus, neck pain, and shoulder pain.

Figure 1:
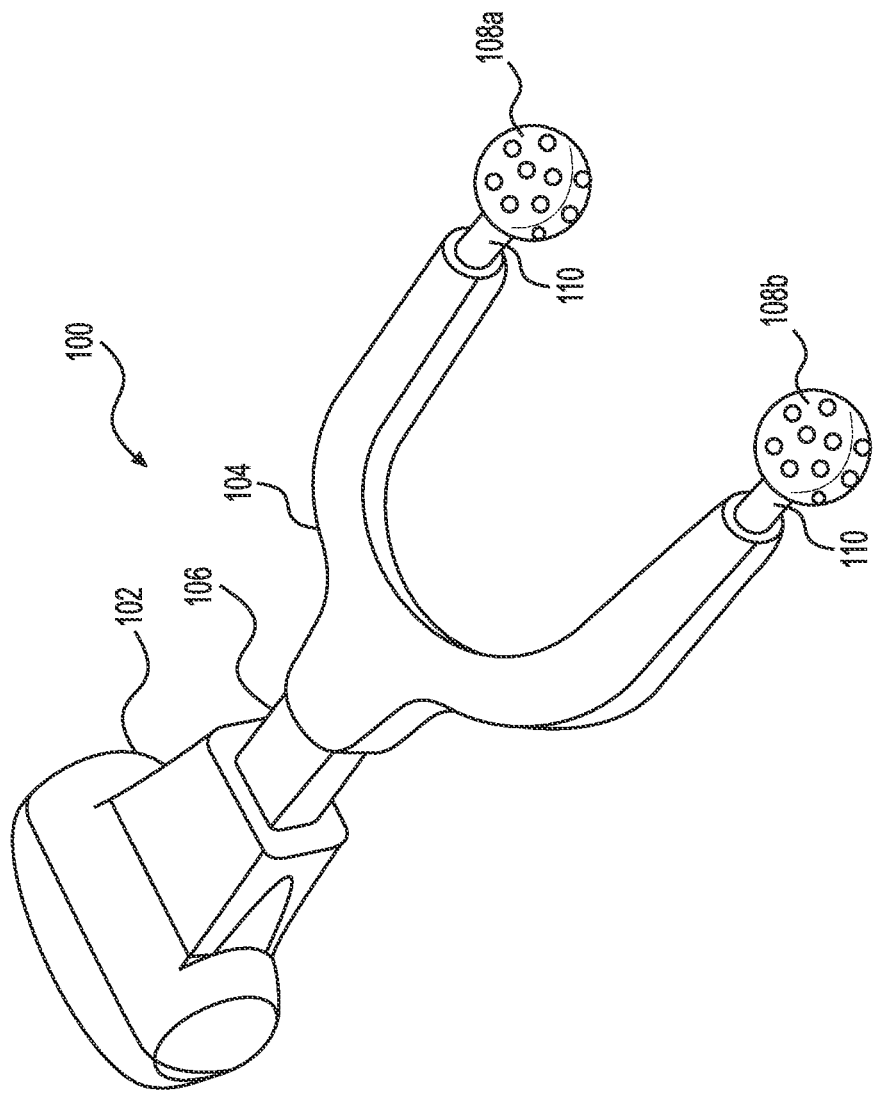
FIG. 1 depicts a front perspective view of an illustrative intraoral phototherapy device according to one aspect of the disclosure.
Figure 2:
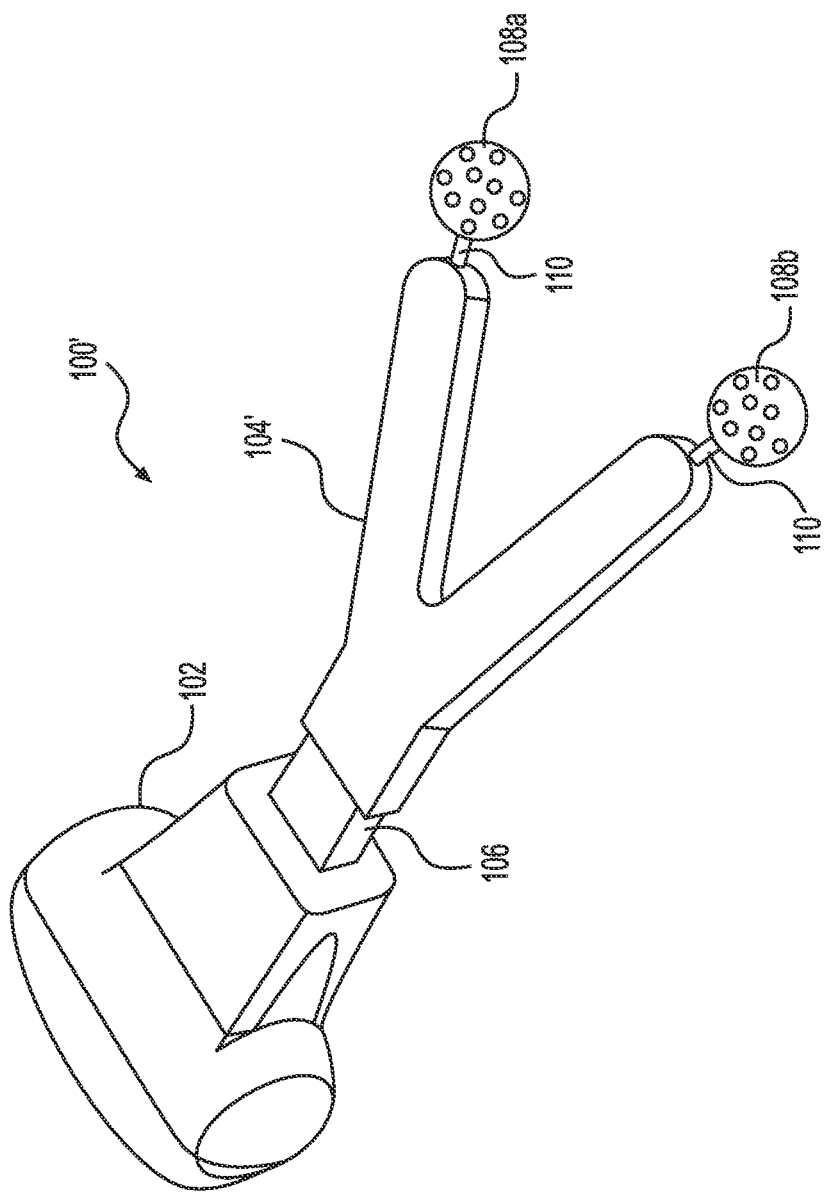
FIG. 2 depicts a front perspective view of a further exemplary embodiment of an intraoral phototherapy device.
Figure 3:
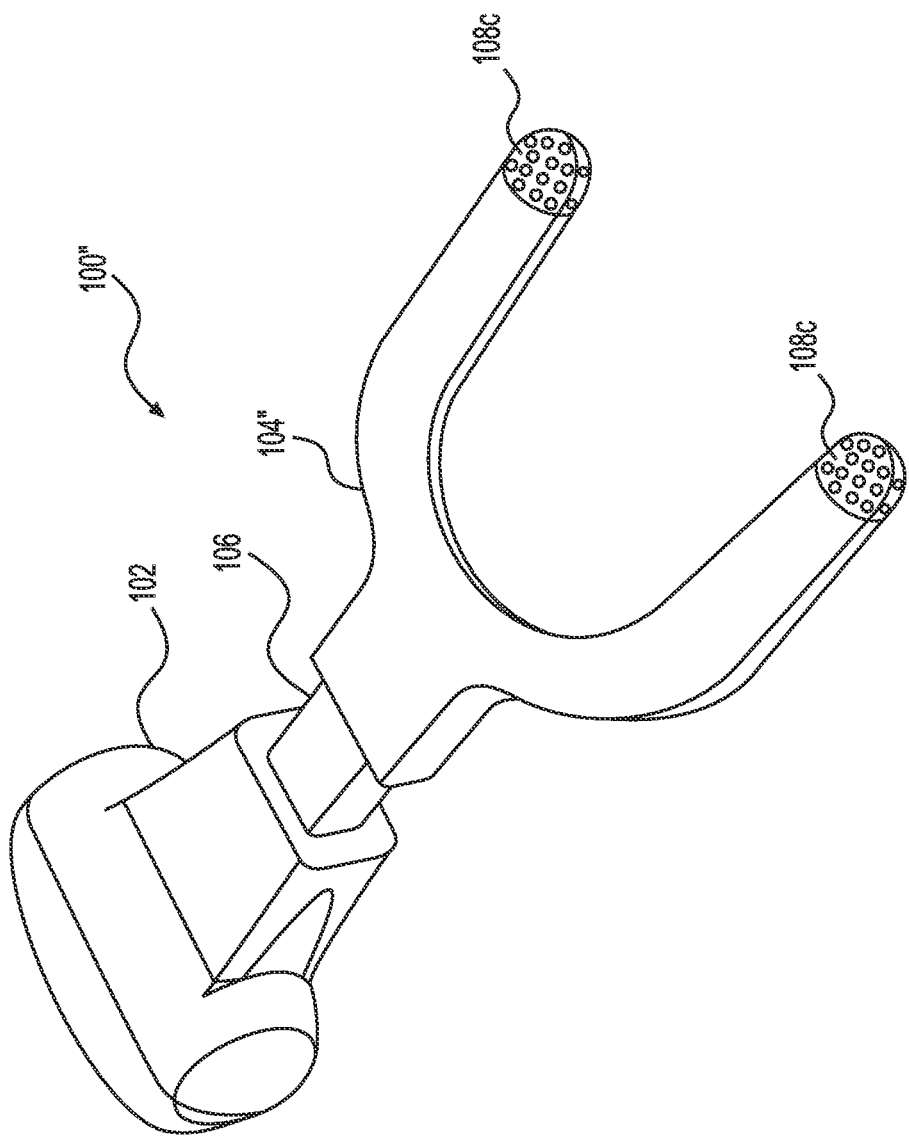
FIG. 3 depicts a front perspective view of yet a further exemplary embodiment of an intraoral phototherapy device.
Figure 4:
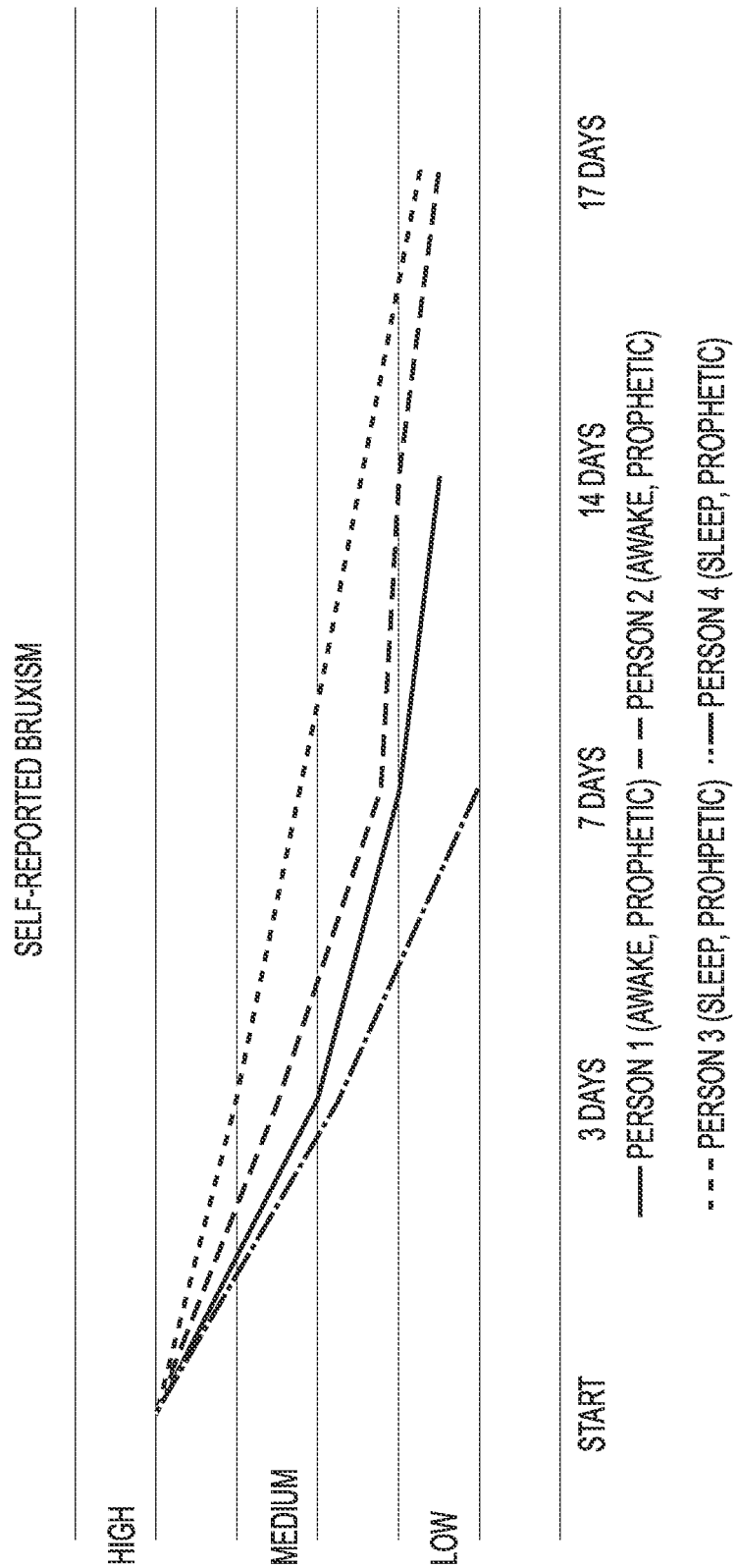
FIG. 4 is a chart showing the effects over time on patient-reported bruxism while using phototherapy.

In one aspect, with reference to FIGS. 1-3, use of the phototherapy device providing LLLT or LED light sources for 5 minutes daily can decrease the incidence of sleep and awake bruxism. For the treatment of sleep bruxism, the treatment can take place while awake, for example before bedtime. Without being bound by theory, the light from the phototherapy stimulates organization of soft tissues by entering the cell mitochondria, being absorbed by the chromophores, and elevating cellular activity. Therefore, it is believed that the increased circulation of the transport of oxygen, lymphatic flow, and immune cells enhance the cell's ability to fight infection, decreasing inflammation and accelerating the healing process to improve oral health. Accelerated healing and cellular organization result in better pain management for the patient because of its ability to reduce inflammation while also advantageously exhibiting regenerative and analgesic effects. The result is lower incidence of bruxism compared to than without treatment.

An intraoral phototherapy device, as indicated, may be utilized immediately before sleep following a guidance procedure related to sleep bruxism treatment. In an aspect, with reference to FIGS. 1 and 2, use of the device 100 providing light therapy for 5 minutes daily, increases the circulation, releases the inflammation of the muscles and jaw, decreases the muscle pain and tension, relaxes the muscles, therefore relieves anxiety and stress, and assist in correcting and treating bruxism.

An intraoral phototherapy device, as indicated, may be utilized immediately after sleep following a guidance procedure related to bruxism treatment. In an aspect, with reference to FIGS. 1-3, use of the device 100 provides light therapy for 5 minutes daily, relieving the stress of the muscles around the TMJ area, relieving the pain of the muscles and decreasing the potential risk of developing TMD.

An intraoral phototherapy therapy according to the present disclosure is also advantageously configured to help alleviate bruxism in patients receiving medical treatments tending to increase the incidence of bruxism. In an aspect, patients receiving anti-depressants such as fluoxetine and paroxetine can be treated with LLLT or LED therapy to help combat these drugs' correlation with increased bruxism.

Described herein are intraoral phototherapy devices, which in certain embodiments include a mouthpiece configured to transmit light radiation to all or a portion of the patient's treatment area proximally to the hamular notch of the maxilla or the retromolar pad of the mandible.

Figure 5:
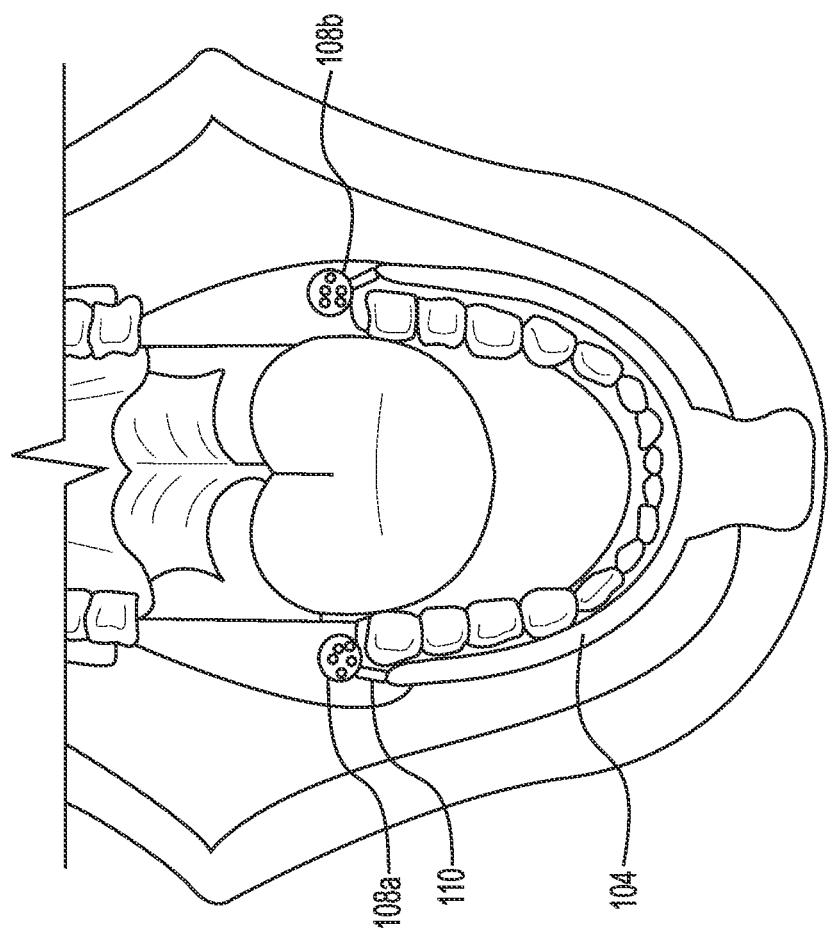
FIG. 5 depicts an illustrative intraoral phototherapy device, such as that depicted in FIG. 1 placed in the mouth of a user, according to one aspect of the disclosure.
Figure 6:
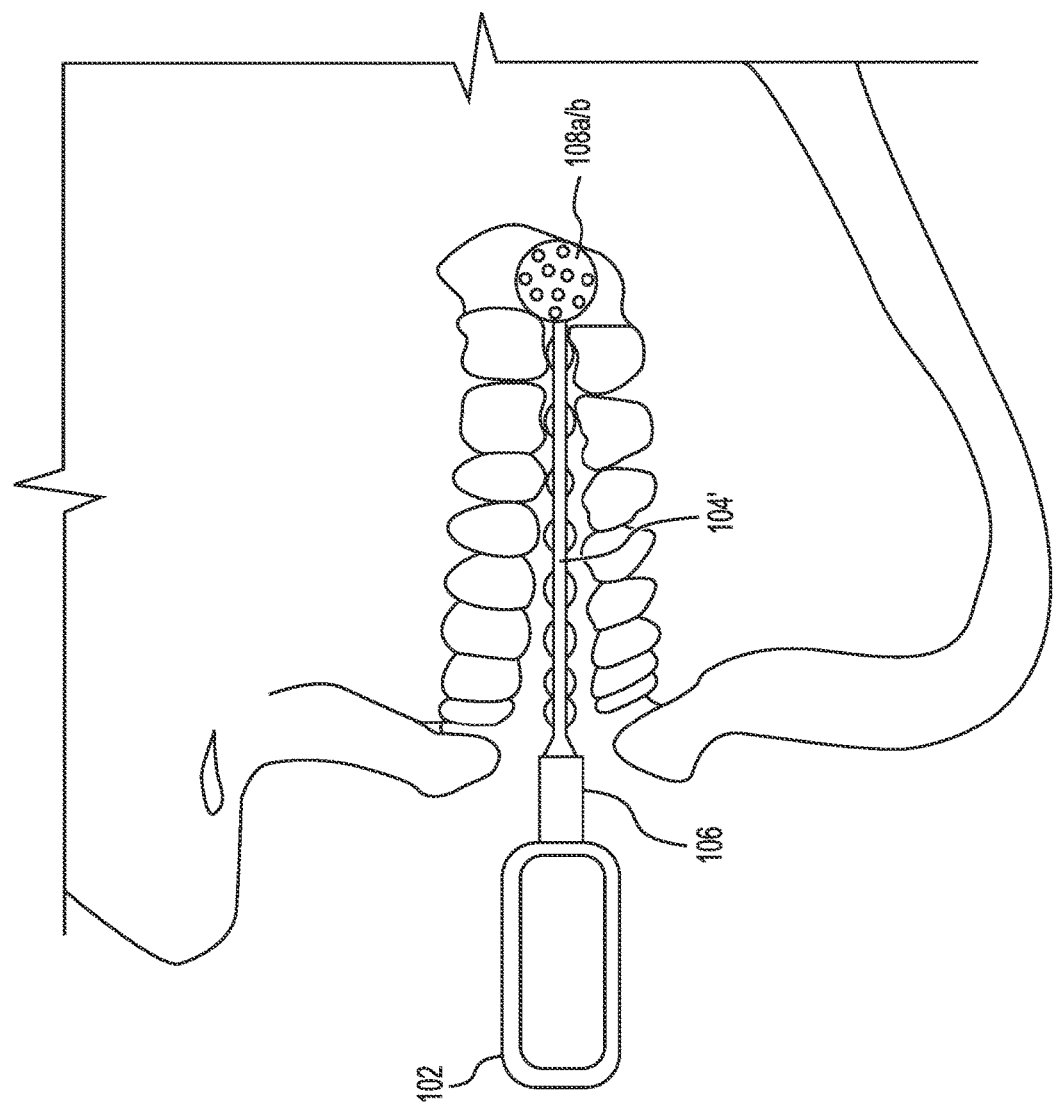
FIG. 6 depicts an illustrative intraoral phototherapy device, such as that depicted in FIG. 2 placed in the mouth of a user, according to one aspect of the disclosure.

Referring to FIGS. 1-3, an exemplary dental device 100, 100', 100" includes a mouthpiece 104, 104', 104" operatively connected to a housing 102 via connector 106. The housing can contain various operational components as described further below. The mouthpiece 104, 104', 104" can be separable from the housing 102 for interchangeability between users or for ease of cleaning. The mouthpiece 104, 104', 104" can be placed between the teeth and/or the cheeks as shown in FIG. 5 or the mouthpiece 104, 104', 104" can be bitten by the occlusal of the teeth as shown in FIG. 6. The mouthpiece 104, 104', 104" can include one or more oral tissue-contacting portions, such as a probe for contacting muscles towards the back of the mouth, gums, teeth, or other oral tissues.

As shown in FIGS. 1-2, the mouthpiece 104, 104' can be connected to a light emitter tips 108a, 108b by a connector 110. The configuration of the connector 110, such as the length, can be appropriately adjusted by a telescopic structure or other arrangements known in the art, as well as the angular orientation of the emitters with respect to the mouthpiece 104, 104'. The emitters 108a, 108b can be appropriately shaped such as ball shape or oval shape to distribute light to the hamular notch of the maxilla or the retromolar pad of the mandible, which are located at the back of the mouth. As shown in FIG. 3, emitters 108c can also be immovably formed as part of the mouthpiece 104". Other shapes for the mouthpiece 104, 104', 104" and emitters 108a, 108b, 108c and tip 104 are possible. Emitters 108a, 108b, 108c can also be formed of compressible material to allow flexible fitment between oral structures.

A light source can be located in the mouthpiece 104, 104', 104" or the housing 102 to send the light to the light emitting tips 108a, 108b, 108c. The housing 102 can also include the electronics to control the light emitting, collect usage and device operation data, collect data from sensors in the mouthpiece or base, and store data in memory. The housing 102 can further include various operational components such as a power supply, data storage, microcontroller, timer, on-off switch, data connector, wireless communications, etc. The housing 102 can include a data interface, which can be wired or wireless, to allow a data connection to other devices. The housing 102 can also include a power interface to allow charging of any onboard power sources, such as batteries or capacitor banks. The mouthpiece 104, 104', 104" can be electrically interconnected to the housing 102 via connector 106. The configuration of the connector 106, such as the length and angular orientation of the housing 102 with respect to the mouthpiece 104, can be appropriately adjusted. The light source can either be embodied in emitters 108a, 108b, 108c or as a light source in the housing 102 with light channels such as fiber optics conveying radiation to the emitters 108a, 108b, 108c. The mouthpiece of the dental device 100 can, as described above, be sized and shaped to contact any oral tissue, including some or all of the muscle tissues, specific regions of the TMJ, or both.

In some embodiments, the patient can be instructed to use the appliance for a prescribed time to treat an oral tissue site. For example, the patient can be instructed to use the appliance for example, five minutes daily, over a period of time, for example four months.

Light emitting can be applied in multiple directions or selected to be primarily in a single direction. The primary anatomical reference directions with reference to a standing human are superior-inferior (up and down), anterior-posterior (front to back), medial-lateral (side to side). Because stressed muscles by bruxism places pressure on oral structures located primarily in the anterior-posterior plane behind the molar teeth, it may be advantageous to choose light emitters directing radiation in the anterior-posterior direction either separately or in combination.

Intraoral Photothrapy Devices

According to an aspect of the present disclosure, an intraoral phototherapy device that provide light emitters at one or more predetermined wavelength is provided. In some embodiments the light wavelength is fixed within a lower bound and an upper bound. The lower bound can be greater than about 700 nm, 690 nm, 680 nm, 670 nm, 660 nm, 650 nm, 640 nm, 630 nm, 620 nm, 610 nm, 600 nm, or less. The upper bound can be greater than about 900 nm, 910 nm, 920 nm, 930 nm, 940 nm, 950 nm, 960 nm, 970 nm, 980 nm, 990 nm, 1000 nm, or more. In some embodiments, the wavelength varies within a lower and an upper bound. In some embodiments two or more wavelength, fixed or varying, are employed.

In some embodiments the duration of a treatment session can be specified to be greater than about 30 seconds, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, or more; or specified to be less than about 20 min, 19 min, 18 min, 17 min, 16 min, 15 min, 14 min, 13 min, 12 min, 10 min, 9 min, 8 min, 7 min, 6 min, 5 min, 4 min, 3 min, 2 min, 1 min, 30 seconds, or less.

FIG. 1 depicts an intraoral phototherapy device according to an example. The intraoral phototherapy device 100 can include a mouthpiece 104. A light source is provided to deliver radiation to light emitting tips on the mouthpiece 104, attached by the connector 110, including a plurality of light emitters 108a, 108b disposed on the tips of the mouthpiece 104. The mouthpiece 104 can be configured to be provided along the buccal side of a user's mouth, or the mouthpiece 104 can be provided between the occlusal surfaces of a user's teeth, and to be bite down during the treatment. The mouthpiece 104 can be adjusted by the user to locate the stressed and/or painful facial muscles during the treatment. The mouthpiece 104 is configured to cover at least the hamular notch of the maxilla or the retromolar pad of the mandible and part of the facial muscles is desired. The light source is configured to provide light to light emitters through fiber optics or light guides at one or more preset wavelengths and intensities or can be configured as light-emitting elements such as LEDs mounted on the mouthpiece 104.

To achieve the maximum desired results in muscle recovery, further studies are needed to optimize the parameters of phototherapy. Such parameters may include wavelength, intensity, and dosage. Dosage may include duration per use, number of uses per day, or number of days of use, either consecutively or at a certain schedule.

In some embodiments, light may be administered by the phototherapy device. The phototherapy device, when in use, may be configured to provide light at a wavelength as disclosed herein. The phototherapy device, when in use, may be further configured to provide light at an intensity range. In some embodiments, the mouthpiece of a phototherapy device can have an intensity within a lower bound and an upper bound. The lower bound can be greater than about 20 mW/cm$^2$, 25 mW/cm$^2$, 30 mW/cm$^2$, 35 mW/cm$^2$, 40 mW/cm$^2$, 45 mW/cm$^2$, 50 mW/cm$^2$, 55 mW/cm$^2$, 60 mW/cm$^2$, or more; or less than about 60 mW/cm$^2$, 55 mW/cm$^2$, 50 mW/cm$^2$, 45 mW/cm$^2$, 40 mW/cm$^2$, 35 mW/cm$^2$, 30 mW/cm$^2$, 25 mW/cm$^2$, 20 mW/cm$^2$, or less. The upper bound can be greater than about 155 mW/cm$^2$, 160 mW/cm$^2$, 165 mW/cm$^2$, 170 mW/cm$^2$, 175 mW/cm$^2$, 180 mW/cm$^2$, 185 mW/cm$^2$, 190 mW/cm$^2$, 195 mW/cm$^2$, 200 mW/cm$^2$, or more; or less than about 200 mW/cm$^2$, 195 mW/cm$^2$, 190 mW/cm$^2$, 185 mW/cm$^2$, 180 mW/cm$^2$, 175 mW/cm$^2$, 170 mW/cm$^2$, 165 mW/cm$^2$, 160 mW/cm$^2$, 155 mW/cm$^2$, or less.

In some embodiments, sensors (not shown) may be added to the intraoral phototherapy device, either on the light source device or on the mouthpiece. The sensors may be configured to detect and monitor the parameters of the light, for example, wavelengths, intensities, and dosage. The sensors may also be configured to detect if the user has positioned the mouthpiece correctly. The sensors may be photoresistors, infrared sensors, reflectance sensors, proximity sensors, pressure sensors, humidity sensors, temperature sensors, or any combination of them.

In some embodiments, the mouthpiece could be in contact with at least one part of the muscle near which pain relief and relaxation is needed. In some embodiments, the mouthpiece includes the light fibers or guides may be configured to be placed along the buccal mucosa between the outer surface of the teeth and cheeks. In some embodiments, the mouthpiece includes the light fiber or guides in a shell that can be clamped down by both occlusal surfaces, leaving the distal end out of the bite and placed in the back of the mouth. The shape of the mouthpiece can be customized to cover only a selected area or a larger general area. In some embodiments, the mouthpiece may be configured to be retractable to treat different locations of the facial muscles.

In some embodiments, the distal end of the distal end of the mouthpiece may be configured to be placed in contact with the hamular notch of the maxilla or the retromolar pad of the mandible at the user's back of the mouth, between and clamped by the molar surfaces and cheek. In some embodiments, the distal end of the mouthpiece can cover the entire or only a part of the muscles. The shape of the distal end of the mouthpiece can be a ball shape, an oval shape, or customized to cover only a selected area or a larger general area.

According to yet another aspect of the present disclosure, a method for the treatment of bruxism is described. The method includes providing an intraoral phototherapy device, comprising a base including a light source, and light guides or fiber optics extending from the base and delivering light to the distal end of the mouthpiece, configured to treat at least a portion of muscles and at least a portion of gum and teeth of gum.

Method for Treating Bruxism

According to yet another aspect of the present disclosure, a method for the treatment of sleep and/or awake bruxism is described. The method includes providing the mouthpiece of the intraoral phototherapy device to a user and providing instructions to the user. The instruction may include placement guidelines and dosage information. The dosage information may include the duration of each treatment session, the number of sessions in a day, the number of days, etc. For example, the instruction may instruct a user to use the intraoral phototherapy device for number of times per day. In some embodiments the treatment frequency can be specified to be once per day, twice per day, 3 times per day, 4 times per day, 5 times per day, 6 times per day, 7 times per day, 8 times per day, 9 times per day, or more. In some embodiments the duration of treatment can be specified to be about 1 day, 1 week, 2 weeks, 3 weeks, 1 month, 2 months, 3 months, 4 months, 5 months, 6 months, 7 months, 8 months, 9 months, 10 months, 11 months, 1 year, or more.

In some embodiments, the method may further include configuring the light source to provide a light emitting to the distal end of the mouthpiece. The LLLT or LED light may eventually be applied to the hamular notch of the maxilla or the retromolar pad of the mandible proximally to the TMJ through the mouthpiece. The light emitting (e.g., wavelengths, intensities, etc.) can be adjusted by selecting preset values or fine-tuned by users, technicians, or healthcare professionals.

According to yet another aspect of the present disclosure, a method for the treatment of bruxism is described. The method includes steps of identifying a sleep and/or awake bruxism symptom, for example sore and tight muscles around the jaw and TMJ, applying a light stimulus to a portion of the treatment site, sensing a baseline response at the treatment site, applying one or more light sessions over a period of time, sensing at least one second response at the treatment site, and determining an inflammation status based on a comparison between the baseline response and one or more second responses. Inflammation status could be detected using numerous modalities, including, for example, direct observation, reflectometry, etc. In some embodiments, the method may further include applying a stimulus based on detected inflammation status.

In some embodiments, the stimulus applied can be one or light energy, electrical energy, or a mechanical dynamic load that is either isotonic or isometric. In addition, the stimulus can be applied to a portion of the facial muscles, teeth, and/or gum tissues symmetrically or asymmetrically on one side of the facial site or across the facial site, such as across the tooth side and lingual side, or the mesial side and distal side. In some embodiments, sensing a baseline response can include information informing an inflammation status on the buccal mucosa side.

EXAMPLES

The following examples are showing sleep and awake bruxism decreasing over time with use of the phototherapy device.

Example 1

A patient uses the intraoral phototherapy device at 800 nm wavelength, applies for 1 session (5 minutes) in the morning and repeats daily in the evening. During an acute incident of awake bruxism, a 3rd session of the phototherapy is added at the peak of awake bruxism to aid in breaking the cycle. An immediate decrease in muscle tension and related soreness can be noted after each session of the phototherapy with improvement in comfort and less associated pain. Following 3 days of use twice daily, a lower incidence of awake bruxism is noted and when occurring, the magnitude is lower. After 14 days of use twice daily, the incidence of awake bruxism can be greatly reduced and is of lower magnitude, then the usage can be switched to once-daily as maintenance. When an acute episode occurs an additional session of phototherapy is added at the time of the incident or as soon as is practical.

Example 2

A patient uses the intraoral phototherapy device as above for 2½ weeks. He has utilized an orthotic mandibular repositioning device to increase airway space, decreasing sleep apnea. This sleep appliance prevents night-time clenching but cannot be worn during the day when clenching is noted. After the first use of the phototherapy device, there is an immediate decrease in discomfort in the masseter muscles, where the primary effect of clenching is observed. With twice-daily five-minute usage, the patient notes reduced or eliminated discomfort in the musculature.

Example 3

A patient is diagnosed with sleep bruxism. Waking phototherapy is utilized by the patient daily. The patient notes no pain following treatment. The incidence of sleep bruxism decreases over time. Phototherapy application is maintained to preserve the decrease in incidence of sleep bruxism.

The patient uses phototherapy at 800 nm, initially applies for 1 session (5 minutes) in the morning and repeats in the evening daily. An immediate decrease in muscle tension and related soreness is noted after each session of phototherapy with improvement in comfort and less associated pain. Following 3 days of use twice daily, it is noted a lower incidence of sleep bruxism. After 14 days of daily use twice daily, the incidence of awake bruxism is greatly reduced and was of lower magnitude, with an attendant decrease in orofacial pain.

Example 4

A patient is diagnosed with bruxism and is suffering from the facial muscle discomfort associated with bruxism, which developed into a chronic TMJ issue with a limited mouth opening. The phototherapy device is utilized by the patient for 5 minutes per day for a week. The patient can note a reduction in bruxism, an improvement in sleep quality, and a relief of muscle pain around the TMJ. The mouth opening increases can be noted after 1 week of usage of the phototherapy device.

The foregoing descriptions have been presented for purposes of illustration. They are not exhaustive and are not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps or inserting or deleting steps.

It should be noted that, the relational terms herein such as "first" and "second" are used only to differentiate an entity or operation from another entity or operation, and do not require or imply any actual relationship or sequence between these entities or operations. Moreover, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

As used herein, unless specifically stated otherwise, the terms "and/or" and "or" encompass all possible combinations, except where infeasible. For example, if it is stated that a database may include A or B, then, unless specifically stated otherwise or infeasible, the database may include A, or B, or A and B. As a second example, if it is stated that a database may include A, B, or C, then, unless specifically stated otherwise or infeasible, the database may include A, or B, or C, or A and B, or A and C, or B and C, or A and B and C.

It is appreciated that the above-described embodiments can be implemented by hardware, or software (program codes), or a combination of hardware and software. If implemented by software, it may be stored in the above-described computer-readable media. The software, when executed by the processor can perform the disclosed methods. The computing units and other functional units described in this disclosure can be implemented by hardware, or software, or a combination of hardware and software. One of ordinary skill in the art will also understand that multiple ones of the above-described modules/units may be combined as one module/unit, and each of the above-described modules/units may be further divided into a plurality of sub-modules/sub-units.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the disclosure disclosed herein. It is intended that the specification and examples be considered as exemplary only, with a true scope and spirit of the disclosure being indicated by the following claims. It is also intended that the sequence of steps shown in figures are only for illustrative purposes and are not intended to be limited to any particular sequence of steps. As such, those skilled in the art can appreciate that these steps can be performed in a different order while implementing the same method.

What is claimed is:

1. A method for treatment of bruxism, comprising:
    identifying a patient having bruxism;
    providing to the patient an intraoral phototherapy device having a flexible mouthpiece for directing the light to the treatment area; and
    providing instructions for using the intraoral phototherapy device, the instructions comprising:
        placing and adjusting the mouthpiece over the treatment area;
        applying a light therapy during a predetermined number of sessions throughout a predetermined treatment period to the patient while awake; and
        removing the flexible mouthpiece from the treatment area;
    wherein the incidence of bruxism is less after removing than without phototherapy treatment.

2. The method of claim 1, wherein the light source includes a light emitting diode (LED).

3. The method of claim 1, wherein the light source includes a plurality of emitters.

4. The method of claim 1, wherein the light source includes a laser.

5. The method of claim 4, wherein the laser source includes a low-level laser.

6. The method of claim 1, wherein a wavelength of the light source is ranging from 600 nm to 1000 nm.

7. The method of claim 1, wherein an intensity of the light source is ranging from 20 mW/cm$^2$ to 200 mW/cm$^2$.

8. The method of claim 1, wherein the session time is from 30 seconds to 20 minutes.

9. The method of claim 1 where sessions are repeated daily/every other day/semi-weekly/weekly.

10. The method of claim 1, wherein the treatment period is from 1 day to 1 year.

11. The method of claim 1, wherein the bruxism treated is awake bruxism.

12. The method of claim 1, wherein the bruxism treated is sleep bruxism.

13. The method of claim 1, wherein the mouthpiece comprises retractable arms that can be adjusted based on the oral cavity size.

14. The method of claim 1, wherein the distal end of mouthpiece comprises a rounded light radiation probe.

15. The method of claim 1, further comprising:
    determining if the actual wavelength or intensity is above or below the set wavelength or the set intensity while the mouthpiece is treated against the facing side of the patient's muscle; and
    adjusting the actual wavelength or actual intensity based upon the determination.

16. The method of claim 1, further comprising:
    monitoring the incidence of bruxism in the patient; and
    adjusting the dosage or parameters of the LLLT or LED based upon the results of the monitoring.

17. A method for treatment of bruxism, comprising:
- identifying a patient having undergone a bruxism symptom proximally to the hamular notch of the maxilla and/or the retromolar pad of the mandible for treating sore and tight muscles;
- providing the patient an intraoral phototherapy device having a flexible mouthpiece for directing the light to the treatment area; and
- providing instructions for waking using the intraoral phototherapy device, the instruction comprising:
  - placing and adjusting the mouthpiece over the treatment area;
  - applying a light therapy during a predetermined number of sessions throughout a predetermined treatment period to the patient while awake; and
  - removing the flexible mouthpiece from the treatment area;
- wherein the bruxism symptom is decreased faster after removing than without phototherapy treatment.

* * * * *